(12) United States Patent
Boratyński et al.

(10) Patent No.: US 8,623,998 B2
(45) Date of Patent: Jan. 7, 2014

(54) METHOD OF PRODUCTION OF POLYANIONIC DRUG-CARRIER CONJUGATES

(75) Inventors: Janusz Boratyński, Wroclaw (PL); Mohamed Salah Omar Megahed, Menoufiya (EG); Urszula Kańska, Jelenia Góra (PL); Dmitry Nevozhay, Houston, TX (US); Joanna Wietrzyk, Wroclaw (PL)

(73) Assignee: Instytut Immunologii I Terapii Doswiadczalnej Pan, Wroclaw (PL)

( * ) Notice: Subject to any disclaimer, the term of this patent is extended or adjusted under 35 U.S.C. 154(b) by 73 days.

(21) Appl. No.: 13/121,295

(22) PCT Filed: Oct. 23, 2009

(86) PCT No.: PCT/PL2009/050031
§ 371 (c)(1),
(2), (4) Date: Jun. 13, 2011

(87) PCT Pub. No.: WO2010/047607
PCT Pub. Date: Apr. 29, 2010

(65) Prior Publication Data
US 2011/0245466 A1    Oct. 6, 2011

(30) Foreign Application Priority Data
Oct. 26, 2008 (PL) .......................... 386351

(51) Int. Cl.
*C07K 14/00* (2006.01)
(52) U.S. Cl.
USPC ........................................ 530/350

(58) Field of Classification Search
USPC ........................................ 530/350
See application file for complete search history.

(56) References Cited

FOREIGN PATENT DOCUMENTS

WO    WO 2004/052406 A1    6/2004

OTHER PUBLICATIONS

Endo et al. 1987; In vitro cytotoxicity of a human serum albumin-mediated conjugate of methotrexate with anti-MM46 monoclonal antibody. Cancer Research. 47: 1076-1080.*
Kosasih et al. 2000; Characterization and in vitro release of methotrexate from gelatin/methotrexate conjugates formed using different preparation variables. International Journal of Pharmaceuticals. 204: 81-89.*
Sigma-Aldrich, 2013. Buffer Reference Center. www.sigmaaldrich.com/life-science/core-bioreagents/biological-buffers.*
International Search Report issued by the International Searching Authority (ISA/O.E.P.M.) on Sep. 6, 2010 in connection with International Application No. PCT/PL2009/050031.

* cited by examiner

*Primary Examiner* — Karen Cochrane Carlson
(74) *Attorney, Agent, or Firm* — Gary J. Gershik; Cooper & Dunham LLP

(57) ABSTRACT

The invention concerns the method of production of a polyanionic macromolecule which is a protein built, among others, from polar amino acids such as lysine, arginine, aspartic acid, glutamic acid), characteristic in that, as a result of the reaction between amine groups and the cyclic anhydride of dicarboxylic acid, the charge changes towards more negatively charged carrier. This reaction gives rise to better therapeutic properties of macromolecules modified in this way.

2 Claims, No Drawings

METHOD OF PRODUCTION OF POLYANIONIC DRUG-CARRIER CONJUGATES

This application is a §371 national stage of PCT International Application No. PCT/PL2009/050031, filed Oct. 23, 2009, designating the United States and claiming priority of Polish Patent Application PL 386 351, filed Oct. 26, 2008, the contents of all of which are hereby incorporated by reference into this application.

The subject of the invention is the method of production of polyanionic macromolecules as drug carriers. The invention concerns conjugates as potent anticancer pharmaceuticals.

Conjugates are used in clinical trials of different phases: in therapy and clinical diagnostics of cancer (mainly hematological) conjugates of antibodies or their fragments with isotopes, for example $^{131}$I and $^{90}$Y, are applied. Drugs forming complexes or conjugates with carriers may have many new, beneficial features. Drug in such a form entering the cell can bypass natural mechanisms of drug resistance and have changed lifetime. Side effects can be altered.

A model drug used in the studies is methotrexate. Methotrexate can be chemically bound with both natural and synthetic carriers. Conjugate of human albumin with methotrexate is currently in advanced clinical trials. This conjugate contains one molecule of methotrexate hound to one molecule of albumin. Conjugates containing more than one molecule of methotrexate bound to one molecule of albumin were toxic. Methods of production of methotrexate conjugates can be found in Polish patent descriptions. Patent PL130458 describes conjugates of methotrexate with fibrinogen. The method of production of conjugates of proteins with drugs in non-aqueous medium was described in patent PL198235. A method of modification of a dicarboxylic molecule was described in patent PL195813. In our studies we confirmed that with the increase of the ratio of methotrexate to protein, the conjugates toxicity increases, however only to a certain level of methotrexate content.

The aim of the invention is providing a method to obtain conjugates of drugs with proteins which would have higher anticancer activity measured, among other parameters, by a significant increase of mean survival time of cancer hearing animals. Unexpectedly it was found that the increase of the degree of substitution above the "toxicity range" gave rise to active anticancer compounds. Anticancer activity is shown by conjugates with low degree of substitution containing 1 mole of methotrexate per approx. 70 kDa of protein, then follows the range of toxic conjugates. Further increase of the ratio of methotrexate to protein up to 1 mole MIX per 1.8-6 kDa of protein unexpectedly gives rise to conjugates with high anticancer activity.

The subject of the invention are conjugates highly substituted with methotrexate as potent anticancer drugs.

The invention concerns the method of production of a polyanionic macromolecule which is a protein built, among others, form polar amino acids (such as lysine, arginine, aspartic acid, glutamic acid), characteristic in that, that as a result of the reaction between amine groups and the cyclic anhydride of dicarboxylic acid, the charge changes towards more negatively charged carrier. This reaction gives rise to better therapeutic properties of macromolecules modified in this way. The reaction is carried out in a buffered aqueous solution in the range of pH 5.5-10 in the presence of organic solvent and excess of dicarboxylic anhydride in the ratio of 0.2-5 moles of methotrexate anhydride per 1 kDa of carrier protein. The reaction product is a polyanion built of chemically modified protein containing attached drug.

The method of modification of the carrier protein with a dicarboxylic molecule anhydride is based on addition of the dicarboxylic molecule to the macromolecule being modified. The modification results in changing the charge of the macromolecule.

One of the ways of improving therapeutic properties of drugs is binding them with synthetic polymers or biological macromolecules. The drugs can be hound covalently with the carriers or form complexes.

The role of the carrier is adding selectivity to the drug. Therapeutic compounds attached to antibodies or their parts can be deposited in cells or tissues in such places where target antigens are presented. Besides, complexes and conjugates of antibodies with enzymes, isotopes and haptens such as biotin and fluorescent markers have found diagnostic applications.

Other macromolecules, such as glycoproteins, lipoproteins, fibrinogen, other proteins and synthetic polymers, are used as carriers of therapeutic compounds, genes and diagnostic markers.

Binding which uses in the coupling reaction only one of two carboxylic groups of the drug molecule results in a number of beneficial features of conjugates obtained in this way. The most important properties are higher negative charge and lower hydrophobicity. Due to a high degree of substitution of the carrier with the drug, the same drug dose can be obtained with a less amount of conjugate.

This method can be applied for production of hapten-carrier conjugates, especially for coupling drugs with carrier proteins.

The invention is presented on practical examples not limiting its protection.

EXAMPLE 1

Activation of Methotrexate 45 mg of methotrexate (as free acid) in 1 ml of dimethylformamide was added to 20 mg of dicyclohexylcarbodiimide. After 20 h reaction at +4° C. the precipitate of dicyclohexylurea was removed. The supernatant containing methotrexate anhydride was used directly from the reaction mixture for binding with protein.

EXAMPLE 2

Preparation of Conjugates of Methotrexate with Carriers

Albumin at the concentration of 20 mg/ml was mixed in a buffered medium (pH 4-12) with the solution of methotrexate anhydride in dimethylformamide in various proportions. After 30 min reaction of anhydride with protein, the conjugate was purified by gel filtration on molecular sieve. Methotrexate-albumin conjugate was obtained as a product of the reaction. It was shown that the reaction was most effective in the range of pH 8-10.

EXAMPLE 3

Bovine fibrinogen at the concentration of 10 mg/ml at pH 8.5 was mixed with different amounts of methotrexate anhydride. After 40 min reaction the conjugates were dialysed. It was shown that the degree of substitution depends on the amount of methotrexate anhydride added. Obtained conjugates contained up to 90 moles of methotrexate per mole of fibrinogen.

EXAMPLE 4

Table of survival of mice with P388 leukemia treated with methotrexate-fibrinogen conjugate. Dosage of methotrexate 40 mg/kg.

| Group | Number of mice | ILS (%) | Mean survival rate | S | L | Degree of substitution of fibrinogen with methotrexat |
|---|---|---|---|---|---|---|
| Control | 8 | — | 11.0 | — | — | — |
| Methotrexat | 8 | 36 | 15.0 | — | — | — |
| Methotrexat-fibrinogen conjugate | 8 | 195 | 32.5 | — | 3 | 57 |
| Methotrexat-fibrinogen conjugate | 8 | 164 | 29.0 | 1 | 2 | 94 |
| Methotrexat-fibrinogen conjugate F-MTX | 8 | 123 | 24.5 | 2 | 4 | 51 |
| Methotrexat-fibrinogen conjugate F-MTX | 8 | 214 | 34.5 | 1 | — | 90 |
| Methotrexat-fibrinogen conjugate G-MTX | 8 | 445 | 60.0 | 5 | 1 | 55 |
| Methotrexat-fibrinogen conjugate G-MTX | 8 | 241 | 37.5 | 2 | 2 | 93 |

S-number of mice with no leukemia detected on the $60^{th}$ day of the experiment (mice considered cured)
L-number of mice which died before the control
ILS-ILS increase of life span
Conjugates F-MTX were obtained in the reaction of fibrinogen glycation with fructose.
Conjugates G-MTX were obtained in the reaction of fibrinogen glycation with glucose.
Glycation was carried out according to the high temperature procedure.

S—number of mice with no leukemia detected on the $60^{th}$ day of the experiment (mice considered cured)
L—number of mice which died before the control
ILS—ILS increase of life span
Conjugates F-MTX were obtained in the reaction of fibrinogen glycation with fructose.
Conjugates G-MTX were obtained in the reaction of fibrinogen glycation with glucose.
Glycation was carried out according to the high temperature procedure.

Method of Production of Poly Anionic Drug-Carrier Conjugates

The subject of the invention is the method of production of polyanionic macromolecules as drug carriers. The invention concerns conjugates as potent anticancer pharmaceuticals.

Conjugates are used in clinical trials of different phases: in therapy and clinical diagnostics of cancer (mainly hematological) conjugates of antibodies or their fragments with isotopes, for example $^{131}$I and $^{90}$Y, are applied. Drugs forming complexes or conjugates with carriers may have many new, beneficial features. Drug in such a form entering the cell can bypass natural mechanisms of drug resistance and have changed lifetime, Side effects can be altered.

A model drug used in the studies is methotrexate. Methotrexate can be chemically bound with both natural and synthetic carriers. Conjugate of human albumin with methotrexate is currently in advanced clinical trials. This conjugate contains one molecule of methotrexate hound to one molecule of albumin. Conjugates containing more than one molecule of methotrexate bound to one molecule of albumin were toxic. Methods of production of methotrexate conjugates can be found in Polish patent descriptions. Patent PL130458 describes conjugates of methotrexate with fibrinogen. The method of production of conjugates of proteins with drugs in non-aqueous medium was described in patent PL198235. A method of modification of a dicarboxylic molecule was described in patent PL195813. In our studies we confirmed that with the increase of the ratio of methotrexate to protein, the conjugates toxicity increases, however only to a certain level of methotrexate content.

The aim of the invention is providing a method to obtain conjugates of drugs with proteins which would have higher anticancer activity measured, among other parameters, by a significant increase of mean survival time of cancer bearing animals. Unexpectedly it was found that the increase of the degree of substitution above the "toxicity range" gave rise to active anticancer compounds. Anticancer activity is shown by conjugates with low degree of substitution containing 1 mole of methotrexate per approx. 70 kDa of protein, then follows the range of toxic conjugates. Further increase of the ratio of methotrexate to protein up to 1 mole MTX per 1.8-6 kDa of protein unexpectedly gives rise to conjugates with high anticancer activity.

The subject of the invention are conjugates highly substituted with methotrexate as potent anticancer drugs.

The invention concerns the method of production of a polyanionic macromolecule which is a protein built, among others, form polar amino acids (such as lysine, arginine, aspartic acid, glutamic acid), characteristic in that, that as a result of the reaction between amine groups and the cyclic anhydride of dicarboxylic acid, the charge changes towards more negatively charged carrier. This reaction gives rise to better therapeutic properties of macromolecules modified in this way. The reaction is carried out in a buffered aqueous solution in the range of pH 5.5-10 in the presence of organic solvent and excess of dicarboxylic anhydride in the ratio of 0.2-5 moles of methotrexate anhydride per 1 kDa of carrier protein. The reaction product is a polyanion built of chemically modified protein containing attached drug.

The method of modification of the carrier protein with a dicarboxylic molecule anhydride is based on addition of the dicarboxylic molecule to the macromolecule being modified. The modification results in changing the charge of the macromolecule.

One of the ways of improving therapeutic properties of drugs is binding them with synthetic polymers or biological macromolecules. The drugs can be bound covalently with the carriers or form complexes.

The role of the carrier is adding selectivity to the drug. Therapeutic compounds attached to antibodies or their parts can be deposited in cells or tissues in such places where target antigens are presented. Besides, complexes and conjugates of antibodies with enzymes, isotopes and haptens such us biotin and fluorescent markers have found diagnostic applications.

Other macromolecules, such as glycoproteins, lipoproteins, fibrinogen, other proteins and synthetic polymers, are used as carriers of therapeutic compounds, genes and diagnostic markers.

Binding which uses in the coupling reaction only one of two carboxylic groups of the drug molecule results in a number of beneficial features of conjugates obtained in this way. The most important properties are higher negative charge and lower hydrophobicity. Due to a high degree of substitution of the carrier with the drug, the same drug dose can be obtained with a less amount of conjugate.

This method can be applied for production of hapten-carrier conjugates, especially for coupling drugs with carrier proteins.

The invention is presented on practical examples not limiting its protection.

EXAMPLE 1

Activation of Methotrexate 45 mg of methotrexate (as free acid) in 1 ml of dimethylformamide was added to 20 mg of dicyclohexylcarbodiimide. After 20 h reaction at +4° C. the precipitate of dicyclohexylurea Was removed. The supernatant containing methotrexate anhydride was used directly from the reaction mixture for binding with protein.

EXAMPLE 2

Preparation of Conjugates of Methotrexate with Carriers

Albumin at the concentration of 20 mg/ml was mixed in a buffered medium (pH 4-12) with the solution of methotrexate anhydride in dimethylformamide in various proportions. After 30 min reaction of anhydride with protein, the conjugate was purified by gel filtration on molecular sieve. Methotrexate-albumin conjugate was obtained as a product of the reaction. It was shown that the reaction was most effective in the range of pH 8-10.

EXAMPLE 3

Bovine fibrinogen at the concentration of 10 mg/ml 51 pH 8.5 was mixed with different amounts of methotrexate anhydride. After 40 min reaction the conjugates were dialysed. It was shown that the degree of substitution depends on the amount of methotrexate anhydride added. Obtained conjugates contained up to 90 moles of methotrexate per mole of fibrinogen.

EXAMPLE 4

Table, of survival of, mice with P388 leukemia treated with methotrexate fibrinogen conjugate. Dosage of methotrexate 40 mg/kg.

| Group | Number of mice | ILS (%) | Mean survival rate | S | L | Degree of substitution of fibrinogen with methotrexat |
|---|---|---|---|---|---|---|
| Control | 8 | — | 11.0 | — | — | — |
| Methotrexat | 8 | 36 | 15.0 | — | — | — |
| Methotrexat-fibrinogen conjugate | 8 | 195 | 32.5 | — | 3 | 57 |
| Methotrexate-fibrinogen conjugate | 8 | 164 | 29.0 | 1 | 2 | 94 |
| Methotrexat-fibrinogen conjugate F-MTX | 8 | 123 | 24.5 | 2 | 4 | 51 |
| Methotrexat-fibrinogen conjugate F-MTX | 8 | 214 | 34.5 | 1 | — | 90 |
| Methotrexat-fibrinogen conjugate G-MTX | 8 | 445 | 60.0 | 5 | 1 | 55 |
| Methotrexat-fibrinogen conjugate G-MTX | 8 | 241 | 37.5 | 2 | 2 | 93 |

S—number of mice with no leukemia detected on the 60$^{th}$ day of the experiment (mice considered cured)
L—number of mice which died before the control
ILS—ILS increase of life span
Conjugates F-MTX were obtained in the reaction of fibrinogen glycation with fructose.
Conjugates G-MTX were obtained in the reaction of fibrinogen glycation with glucose.
Glycation was carried out according to the high temperature procedure.

The invention claimed is:
1. A method of modifying fibrinogen, comprising reacting fibrinogen with an excess amount of a dicarboxylic acid anhydride, in a buffered aqueous solution having a pH of 8.5 in the presence of an organic solvent so as to obtain a fibrinogen conjugate containing 1.7-2.8 moles of the dicarboxylic acid anhydride per 10 kDa of fibrinogen.
2. The method of claim 1, wherein the dicarboxylic acid anhydride is methotrexate in the form of an anhydride.

* * * * *

UNITED STATES PATENT AND TRADEMARK OFFICE
CERTIFICATE OF CORRECTION

PATENT NO. : 8,623,998 B2  Page 1 of 1
APPLICATION NO. : 13/121295
DATED : January 7, 2014
INVENTOR(S) : Boratyński et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 121 days.

Signed and Sealed this
Twenty-second Day of September, 2015

Michelle K. Lee
*Director of the United States Patent and Trademark Office*